March 29, 1960 G. TUKACS Plant Pat. 1,924
CREEPING BENTGRASS PLANT
Filed Aug. 19, 1958
FIG. 1.
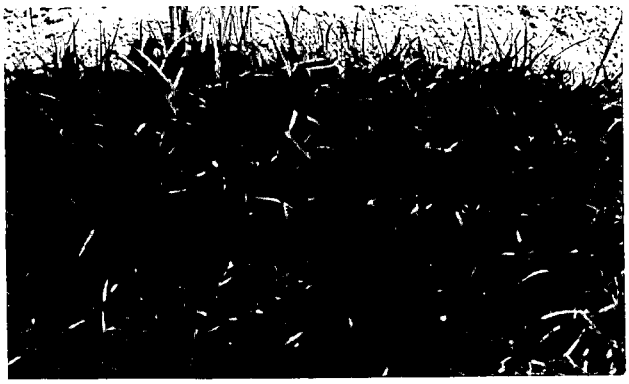
FIG. 2.
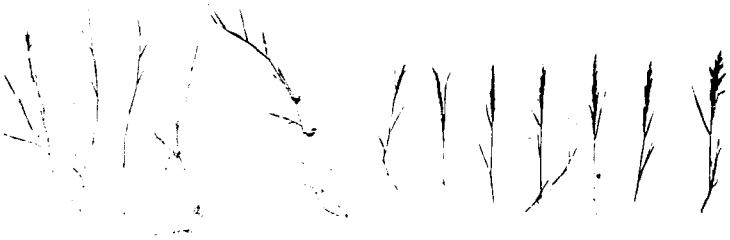
FIG. 3.
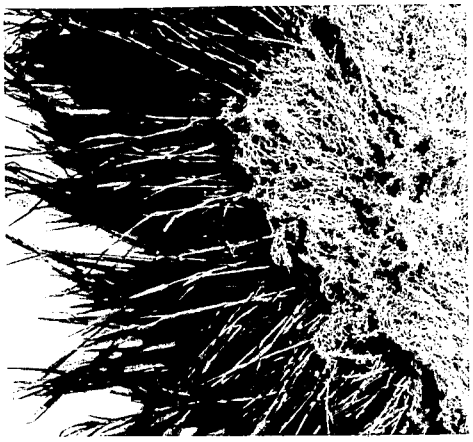
FIG. 4.
INVENTOR
George Tukacs
BY Robbins Cobb
ATTORNEYS United States Patent Office Plant Pat. 1,924
Patented Mar. 29, 1960

1,924

CREEPING BENTGRASS PLANT

George Tukacs, New Milford, Conn., assignor to The Berkshires Grass Company, Inc., New Milford, Conn., a corporation of Delaware Application August 19, 1958, Serial No. 756,053

1 Claim. (Cl. 47—59)

The present invention relates to a new and distinct perennial creeping bentgrass plant which was discovered by me near New Milford, Connecticut as a newly found seedling of unknown parentage.

At the time of my initial discovery, I was hunting for mushrooms in a cultivated area on and around property of my employer in the foothills of the Berkshire Mountains. In a cleft between 2 huge boulders, my attention was attracted to a spot of bright green grass which appeared to be different from any grass I had ever previously seen. Accordingly, my interest therein was aroused to such an extent that I took a clump of the grass plants and set some of the plants in pots. To my great amazement, these specimen plants overflowed the pots within 3 weeks. Subsequent additional plantings in the ground demonstrated a remarkable ruggedness of the grass, as evidenced by the fact that even without the aid of fertilizers, or other chemicals, it thrived through hot summers and endured sub-zero winters.

Continued tests over a period of years showed that my new grass is the first grass to turn green in the spring, stays green longer than most other grasses (until mid-November), makes a lush carpet for at least 7 or 8 months of the year, and stays the same fresh green color even through droughts that parch other grasses. It has also been determined that my grass will grow equally well in brilliant sun, partial sun or shade, or even complete shade under trees. It has survived winter temperatures of 25° below zero weather in Canada, and as much as several weeks of substantially continuous summer heat which went as high as 105° in southern climates. In fact, the new grass is almost indestructible, even by deliberate repeated diggings, since its same healthy vigor persists and permits it to re-establish itself by filling in if it is damaged.

Under normal conditions, a complete lawn of my new grass can be established in approximately 12 weeks after planting. After the first year, if kept cut to approximately ½ inch in length the year round, it will provide the springiest, greenest and most attractive grass that is available.

Asexual reproduction of my new grass by fibrous roots, as well as by stolons, as performed by me at New Milford, Connecticut, shows that the foregoing characteristics come true to form and are established and transmitted through succeeding propagations, and that it is endowed with the following unique combination of characteristics:

(1) An attractive deep chrome-green color, with lavender-pink color around the nodes in sunny locations but absent when grown in the shade, and prolonged color retention from early spring to late fall, particularly in the northern sections of the United States;

(2) Rapid, spreading and luxuriant growth, with attendant ability to choke out weeds;

(3) Wiry leaf blades of sharp-pointed form;

(4) Unusual hardiness under hot, cold and/or dry weather conditions, although it thrives best in the colder climates of the Northern States of the U.S.;

(5) Ease of planting and growth, even in acid and sandy soils;

(6) Medium-fine texture, good springiness, and a self-healing habit when damaged, with consequent ruggedness and good traffic-wearing qualities;

(7) An ability to thrive in both sun and shade;

(8) An ability to grow alone without the aid of nurse grass;

(9) A suitability for close mowing, particularly after the first year; and

(10) Suitability for lawns, golf courses and other sport fields.

In the accompanying drawing, as depicted in color as nearly true as it is reasonably possible to make the same in a color illustration of this character:

Fig. 1 shows a typical plot of my new grass;

Fig. 2 shows typical specimen stolons, with secondary root development from the nodes;

Fig. 3 shows typical seedheads or panicles before anthesis; and

Fig. 4 shows the fibrous, compact, interwoven root system of a typical clump of the new grass.

The following is a detailed description of my new grass, with color terminology in accordance with general color terms of ordinary dictionary significance:

Parentage: Unknown.

Classification: Falls in the Agrostis family and is somewhat related to *Agrostis alba* (redtop), as well as to *Agrostis canina* (velvet bent) and *Agrostis palustris* (creeping bent), and possibly also to *Agrostis tenuis* (colonial bent); some botanists will consider it to be a variety of *Agrostis palustris*, partly because in its early stages, occasional seedheads resemble those of that type grass, but in its anthesis stage, the panicle of my new grass has a pyramidal form characteristic of *Agrostis alba;* while my new grass produces some seedheads or panicles, they ordinarily do not mature and will not reproduce true to form.

Growth: Perennial; rapid (about 40 inches per year, including the stolons); the nodes form stolons and roots which permit a rapid creeping which soon chokes out many weeds and gives fairly complete ground coverage in approximately 12 weeks if single roots are planted about 8 inches apart; likes acid soil; grows well in brilliant sun, partial sun or shade, and/or complete shade; very hardy and withstands extreme heat, cold as low as 25° below zero, and drought, but thrives best in the Northern States.

Leaves: Individual leaves are short, as compared with the normal range for creeping bentgrasses; they are veined on upper side and are sharp-pointed; borne on the culm (which is up to 1.5 mm. wide) in 2 ranks, one at each node; the ligule is of medium length (from 1 to 2 mm. long) and obtuse; blades lax; scabrous on the margins, but otherwise glabrous; blades are more wiry, as well as sharp-pointed, thereby definitely differentiating from colonial bent and creeping bent.

*Length.*—From 3.5 cm. to 8 cm.

*Width.*—From 1.5 mm. to 3 mm.

*Color.*—Bright chrome-green, ranging between light green and blue-green; somewhat lighter than the color of many creeping bentgrasses, but a shade darker than the experimental type of bentgrass known as C-7; color darkens slightly on aging; color appears early in the spring and persists longer than that of most other grasses.

Stolons: Very freely produced; very slender; branching; attain a length of up to 18 inches or more; readily rooting at the nodes.

*Internodes.*—From 2 cm. to 5 cm. long.

*Sheaths.*—Glabrous; usually about ½ as long as the internodes.

*Color.*—Lavender-pink around the nodes; this color is maintained throughout the entire development of my new grass when grown in sunny locations, but is absent when grown in the shade.

Texture: Medium-fine, as compared with many bentgrasses, and completely different from that of velvet bent.

Inflorescence: The flowering acilius is infrequently produced, while the inflorescence is from 4 cm. to 12 cm. long and about 5 mm. wide; dense; most of the short branches are spikelet-bearing to the base, with spikelets about 2 mm. long; glumes subsequal, acute, scabrous on the keels; lemma thin, obtuse, awnless, with palea from ½ to ⅔ as long; in anthesis, the panicle is very similar to that of redtop, only smaller; panicle measures from 3.2 cm. to 13.5 cm. in length and spreads to a pyramidal base about 3.5 cm. wide; much of the time, no seedheads are produced, but when they are, seeds are imperfectly developed, and my new grass is therefore a very poor seed-producer, whereas other types of bentgrass, including colonial bent, produce seed fairly well. Color—in their early development, the floral organs have a pinkish-brick color, turning to a pale-pinkish color while ripening.

Reproduction: Best reproduced asexually from the fibrous roots, but can also be reproduced from the stolons.

I claim:

A new and distinct variety of perennial creeping bentgrass plant, substantially as herein shown and described, characterized particularly as to novelty by the unique combination of attractive deep chrome-green color, with lavender-pink color around the nodes in sunny locations but absent when grown in the shade, and prolonged color retention from early spring to late fall; rapid, spreading and luxuriant growth, with attendant ability to choke out weeds; unusually good hardiness under hot, cold, and dry weather conditions, ease of planting and growth, even in acid and sandy soils; wiry leaf blades of sharp-pointed form; medium-fine texture, good springiness and a self-healing habit when damaged, with consequent ruggedness and good traffic-wearing qualities; the ability to thrive in both sun and shade; the ability to grow alone, without the aid of nurse grass; suitability for close cutting; and suitability for lawns, golf courses and other sport field uses.

No references cited.